United States Patent
Cai et al.

(10) Patent No.: US 12,311,043 B2
(45) Date of Patent: May 27, 2025

(54) LIQUID SUPRAMOLECULAR SELF-RECOGNITION SYSTEM OF LOW-PH AZELAIC ACID, AND PREPARATION METHOD THEREFOR AND APPLICATION THEREOF

(71) Applicant: Wuxi Zhiyan Biotechnology Co., LTD, Wuxi (CN)

(72) Inventors: Beilei Cai, Wuxi (CN); Zhihui Tian, Wuxi (CN); Yue Wang, Wuxi (CN); Zixuan Xu, Wuxi (CN); Shuyan Yang, Wuxi (CN); Liyong Du, Wuxi (CN); Jingguo Yang, Wuxi (CN)

(73) Assignee: Wuxi Zhiyan Biotechnology Co., LTD, Wuxi (CN)

( * ) Notice: Subject to any disclaimer, the term of this patent is extended or adjusted under 35 U.S.C. 154(b) by 0 days.

(21) Appl. No.: 18/978,361

(22) Filed: Dec. 12, 2024

(65) Prior Publication Data
US 2025/0107982 A1    Apr. 3, 2025

Related U.S. Application Data

(63) Continuation of application No. PCT/CN2024/087219, filed on Apr. 11, 2024.

(30) Foreign Application Priority Data

Nov. 15, 2023  (CN) .......................... 202311522018.3

(51) Int. Cl.
| | | |
|---|---|---|
| *A61K 8/362* | (2006.01) | |
| *A61K 8/42* | (2006.01) | |
| *A61K 9/06* | (2006.01) | |
| *A61K 31/194* | (2006.01) | |
| *A61K 31/197* | (2006.01) | |
| *A61K 47/10* | (2017.01) | |
| *A61K 47/18* | (2017.01) | |
| *A61K 47/20* | (2006.01) | |
| *A61Q 19/00* | (2006.01) | |

(52) U.S. Cl.
CPC .............. *A61K 8/362* (2013.01); *A61K 8/42* (2013.01); *A61K 9/06* (2013.01); *A61K 31/194* (2013.01); *A61K 31/197* (2013.01); *A61K 47/10* (2013.01); *A61K 47/183* (2013.01); *A61K 47/20* (2013.01); *A61Q 19/00* (2013.01); *A61K 2800/5922* (2013.01); *A61K 2800/805* (2013.01)

(58) Field of Classification Search
None
See application file for complete search history.

(56) References Cited

U.S. PATENT DOCUMENTS

2016/0144038 A1*  5/2016  Lu .......................... A61K 47/34
                                                                514/772

FOREIGN PATENT DOCUMENTS

| CN | 112521292 A | * | 3/2021 | ............... A61K 8/36 |
|---|---|---|---|---|
| CN | 114569487 A | | 6/2022 | |
| CN | 115463044 A | | 12/2022 | |
| CN | 115919733 A | | 4/2023 | |
| CN | 117045523 A | | 11/2023 | |
| CN | 117551277 A | | 2/2024 | |
| KR | 20080086229 A | | 9/2008 | |
| KR | 20150079144 A | | 7/2015 | |
| KR | 102250875 B1 | | 5/2021 | |
| WO | 2017216722 A2 | | 12/2017 | |
| WO | 2023183563 A1 | | 9/2023 | |
| WO | 2023194557 A1 | | 10/2023 | |

OTHER PUBLICATIONS

Wang Jing Yu: Supramolecular salicylic acid ameliorates rosacea-like eruptions by suppressing NLRP3-mediated inflammasome activation in mice: https://www.sciencedirect.com/science/article/pii/S1567576923003788?via%3Dihubhttps://doi.org/10.1016/j.intimp.2023.110057 (Year: 2023).*
Jakaria Shawon: Molecular Recognition of Azelaic Acid and Related Molecules with DNA Polymerase I Investigated by Molecular Modeling Calculations: Interdiscip Sci Comput Life Sci (2018) 10:525-537 https://link.springer.com/article/10.1007/s12539-016-0186-3 (Year: 2016).*
Laura Vasilica Arseniea et. al. "Azelaic acid-willow bark extract-panthenol—Loaded lipid nanocarriers improve the hydration effect and antioxidant action of cosmetic formulations" Industrial Crops and Products 154 (Jun. 29, 2020) 112658.

* cited by examiner

*Primary Examiner* — Robert A Wax
*Assistant Examiner* — Andre Mach
(74) *Attorney, Agent, or Firm* — IPRO, PLLC

(57) ABSTRACT

Disclosed are a liquid supramolecular self-recognition system of low-pH azelaic acid, and a preparation method therefor and application thereof. The preparation method for the ternary liquid supramolecular self-recognition system of low-pH azelaic acid/succinic acid/panthenol includes the following steps: mixing and heating azelaic acid, succinic acid, and panthenol in a molar ratio of 1:0.5:1-1:10:10 in a sealed container to obtain a mixture and heated at 60-120° C. for more than 1-24 hours, and cooling down the mixture to room temperature after the heating is completed to obtain the liquid supramolecular self-recognition system of low-pH azelaic acid. The preparation method is green and simple, and the resulting supramolecular self-recognition system can effectively improve the solubility of azelaic acid, and have excellent stability without precipitation. In addition, the supramolecular self-recognition system for the azelaic acid/succinic acid/panthenol prepared in the present disclosure is in a liquid form, and can be directly applied to subsequent formulations without special treatment.

8 Claims, 4 Drawing Sheets

LIQUID SUPRAMOLECULAR SELF-RECOGNITION SYSTEM OF LOW-PH AZELAIC ACID, AND PREPARATION METHOD THEREFOR AND APPLICATION THEREOF

TECHNICAL FIELD

The present disclosure belongs to the field of supramolecular technology, and relates to a liquid supramolecular self-recognition system of low-pH azelaic acid, and a preparation method therefor and application thereof.

BACKGROUND

Azelaic acid is a common ingredient used in cosmetics and pharmaceuticals, and is widely applied in skincare and beauty products. Azelaic acid has the effect of inhibiting bacterial growth, especially for the *Propionibacterium* that causes acne, and it can reduce the occurrence of acne and improve existing acne conditions. Azelaic acid can inhibit the production of excessive melanin, thereby reducing skin pigmentation such as freckles and chloasma, making a skin tone more even. Azelaic acid exhibits antioxidant properties, which is conducive to protecting the skin from free radical damage and slowing down the skin aging process. Azelaic acid has an anti-inflammatory effect, and can soothe sensitive skin and reduce redness and irritation. An use amount of azelaic acid in cream cosmetics is usually 15%-20% (mass concentration), but it is difficult for azelaic acid dissolve in water and oil, and azelaic acid has a high melting point, making it lower in solubility, poor in compatibility, and extremely low in bioavailability, which greatly limits the use of azelaic acid. Azelaic acid requires a high concentration for effective application. In a hydrophilic system, azelaic acid tends to precipitate at high concentrations, resulting in unstable system and further generating particles or gravel-like solids in the product system in a product system, thus showing poor compatibility. In an oily system, it is difficult for azelaic acid to form a transparent and stable system due to its compatibility, therefore, excessive oily ingredient and azelaic acid are often used to form cream, which leads to poor product feel and spreadability, and may also cause a heap of side effects.

In the prior art, azelaic acid is subjected to a series of methods such as ultrafine grinding treatment, complexation/co-crystallization with organic bases and azelaic acid, and encapsulation of azelaic acid, so as to improve its solubility. However, these methods are very complicated and require some organic solvents, moreover, the solubility and stability of azelaic acid generated therefrom are not effectively improved. Specifically, the Chinese Patent CN 113248364 A provides a method for improving water solubility of azelaic acid by compounding alkaline substances (such as theophylline, echinacin, carnitine) with azelaic acid to form salt. However, the method requires a large amount of organic solvent and a relatively complicated process. The Chinese Patent CN 114181072 A provides a preparation process for ultra-fine azelaic acid, which improves the water solubility of azelaic acid to some extent, but increases processing costs, and fails to fundamentally solve the problems, that is, fails to greatly improve the solubility of azelaic acid. The Chinese Patent CN 112624918 A provides an azelaic acid cocrystal with an organic base and a preparation method therefor. According to the method, a solid cocrystal is prepared in an organic solvent in an inert gas atmosphere, and a target cocrystal is obtained by a series of operations, such as membrane filtration, recrystallization, and solvent removal. The method is not environmentally friendly, involves a complicated process, and fails to clearly identify a degree of solubility improvement of azelaic acid. The Chinese Patent CN 108187070 A provides a method for preparing an azelaic acid—cyclodextrin inclusion complex by cyclodextrin inclusion and spray drying. Although the method improves the solubility of azelaic acid to some extent, it involves a complicated process and requires a large amount of cyclodextrin, making an inclusion system easy to become sticky and having poor skin feel during use. The Chinese Patent CN 110669226 A discloses a preparation method for a polyethylene glycol/propylene glycol/azelaic acid supramolecular system, which, however, increases the solubility of azelaic acid by 3.33 times only, that is, approximately 8 g/L.

Given the important application and practical value of azelaic acid, a simpler and greener treatment process is still needed, so as to address poor solubility and instability of azelaic acid in a more effective manner.

Supramolecular self-recognition refers to the assembly of multi-molecular aggregates composed of non-covalent bonds. Different molecules are spontaneously connected by non-covalent bonds, such as hydrogen bonds, van der Waals force, and x-x stacking, to form an organic entirety. From a chemistry perspective, molecules forming a supramolecular system remain unchanged, therefore, they can maintain their original efficacy, but the solubility, bioavailability, stability, and the like, of a supramolecular self-recognition system can be significantly improved. However, the choice of compatible molecules is critical for the supramolecular self-recognition system. Types, contents, and the like of the compatible molecules will directly affect the formation of the supramolecular self-recognition system.

SUMMARY

Technical Problems

Azelaic acid has poor water solubility and low stability; and
existing methods for improving the solubility of azelaic acid often involve overly complex processes, and require some organic solvents, and solubility and stability of azelaic acid generated therefrom are not effectively improved.

Technical Solutions

In order to solve the above problems, the present disclosure uses azelaic acid, succinic acid, and panthenol as compatible molecules to form a supramolecular self-recognition system. The preparation process is green and simple, and the resulting supramolecular self-recognition system can effectively improve the solubility of azelaic acid, and have excellent stability without precipitation. In addition, the supramolecular self-recognition system for the azelaic acid/succinic acid/panthenol prepared in the present disclosure is in a liquid form, and can be directly applied in subsequent formulations without special treatment.

The succinic acid used in the present disclosure can effectively regulate a pH value. A lower pH value matches a physiological acid-base balance of human skin, helping to protect the skin from irritation and maintaining normal functions of the skin. Further, the succinic acid can help to inhibit the growth of bacteria and microorganisms and to enhance antiseptic and antibacterial properties of cosmetics.

The succinic acid also has the efficacy of antioxidant, moisturizing, anti-inflammatory, cleansing, conditioning, and the like, imparts multifunctionality to related cosmetic products, and is conducive to improving skin condition, delaying aging, and enhancing texture of products.

The panthenol used in the present disclosure is a derivative of vitamin B5, also known as "pro-vitamin B5". It is mainly used as a lubricant, emollient, and humectant in cosmetics and beauty products. The panthenol can penetrate the skin, enhance lubrication and moisture retention. After the panthenol is absorbed by skin tissue, its alcoholic hydroxyl group is oxidized and converted into pantothenic acid. Pantothenic acid is an important substance synthesizing coenzyme A, which constitutes an essential substance for metabolism in the body, and can promote the metabolism of protein, lipid, and carbohydrates, protect the skin and mucous membranes, and improve hair shine.

A first objective of the present disclosure is to provide a preparation method for a ternary liquid supramolecular self-recognition system of low-pH azelaic acid/succinic acid/panthenol, including the following steps:

mixing and heating azelaic acid, succinic acid, and panthenol to obtain a liquid supramolecular self-recognition system of low-pH azelaic acid.

Further, a molar ratio of the azelaic acid to the succinic acid to the panthenol is 1:0.5:1-1:10:10 (mean 1:0.5-10:1-10).

Further, the mixing and heating are performed in a sealed container.

Further, the mixing and heating are performed at a temperature of 60-120° C. for more than 1 hour, and mixing and heating time is further preferably 1-24 hours.

Further, a mixing and heating atmosphere is an inert atmosphere or natural air conditions, and specifically, the mixing and heating atmosphere is helium, nitrogen, argon, or carbon dioxide or natural air.

Further, the mixing and heating involve heating the mixture while stirring, and a temperature rising rate during the heating is 1-10° C./minute; and during the heating process, the mixture becomes liquid to form a liquid supramolecular self-recognition system, and a stirring speed is 200-1000 rpm.

Further, after the mixing and heating are completed, the mixture needs to be cooled down to room temperature, a cooling rate is 1-10° C./minute, and the room temperature stated herein refers to 20-30° C.

Further, the preparation method for a ternary liquid supramolecular self-recognition system of low-pH azelaic acid/succinic acid/panthenol includes the following steps:

mixing and heating azelaic acid, succinic acid, and panthenol in a molar ratio of 1:0.5:1-1:10:10 (mean 1:0.5-10:1-10) in a sealed container to obtain a mixture, heating the mixture at a temperature of 60-120° C. for more than 1 hour, and cooling down the mixture to room temperature after the heating is completed to obtain the liquid supramolecular self-recognition system of low-pH azelaic acid.

A second objective of the present disclosure is to provide a ternary liquid supramolecular self-recognition system of low-pH azelaic acid/succinic acid/panthenol prepared according to the method in the present disclosure.

Further, the low-pH refers to the situation that a pH value of the ternary liquid supramolecular self-recognition system of low-pH azelaic acid is 2.5-5.5.

Further, infrared spectrum of the ternary liquid supramolecular self-recognition system of low-pH azelaic acid/succinic acid/panthenol has an absorption peak in a range of 3500-3200 cm$^{-1}$ corresponding to an absorption peak of a hydroxyl group (a hydrogen bond), forming a broader peak, and peaks are observed at 1720 cm–1, 3349 cm$^{-1}$, and 1690-1700 cm$^{-1}$, and the like.

Further, a mass fraction of azelaic acid in the ternary liquid supramolecular self-recognition system of low-pH azelaic acid/succinic acid/panthenol can reach 42%.

Further, the ternary liquid supramolecular self-recognition system of low-pH azelaic acid/succinic acid/panthenol can significantly enhance the water solubility of azelaic acid, and can be miscible with water in a specific ratio, such that a mass ratio range of the ternary liquid supramolecular self-recognition system of low-pH azelaic acid/succinic acid/panthenol dissolved in water is 2:1-1:100 (mean 1-2:1-100).

A third objective of the present disclosure is to provide application of the ternary liquid supramolecular self-recognition system of low-pH azelaic acid/succinic acid/panthenol prepared according to the method in the present disclosure in the field of cosmetics or pharmaceuticals.

A fourth objective of the present disclosure is to provide a cosmetic product containing the ternary liquid supramolecular self-recognition system of low-pH azelaic acid/succinic prepared according to the method in the present disclosure.

Further, a use amount of the ternary liquid supramolecular self-recognition system of low-pH azelaic acid/succinic acid/panthenol is 0.5-50% (mass percentage).

Further, the cosmetic product includes serum, treatment essence, spray, skincare foam, lotion, shampoo, and the like.

Further, composition of the cosmetic product includes the following components by mass percentage:

glycerin: 2-4%, butanediol: 2-4%, phenoxyethanol: 0.3-0.5%, caprylyl glycol: 0.3-0.5%, *sphingomonas* sp. fermentation extract: 0.05-0.15%, sodium hyaluronate: 0.04-0.06%, polyacryloyldimethyl taurate salt: 0.05-0.15%, the ternary liquid supramolecular self-recognition system of low-pH azelaic acid/succinic acid/panthenol: 10-30%, white willow bark extract: 1-3%, ethylenediaminetetraacetic acid: 0.04-0.06%, *portulaca oleracea* extract: 1-3%, and with balance being water.

A fifth objective of the present disclosure is to provide a pharmaceutical product containing the ternary liquid supramolecular self-recognition system of low-pH azelaic acid/succinic prepared according to the method in the present disclosure.

Further, a use amount of the ternary liquid supramolecular self-recognition system of low-pH azelaic acid/succinic acid/panthenol is 1-50% (mass percentage).

Further, composition of the pharmaceutical product includes the following components by mass percentage:

the ternary liquid supramolecular self-recognition system of low-pH azelaic acid/succinic acid/panthenol: 10-30%, docusate sodium: 0.03-0.06%, disodium edetate: 0.05-0.15%, glycerin: 3-5%, poloxamer 124:0.1-0.3%, propylene glycol: 3-5%, SIMULGEL 600PHA (acrylamide/sodium acryloyldimethyl taurate copolymer and isohexadecane and polysorbate 80 and sorbitan oleate): 3-5%, and with balance being water.

Further, the pharmaceutical product is gel, spray, liquid preparation, cream, and the like.

A sixth objective of the present disclosure is to provide a method for improving the water solubility and stability of azelaic acid, including the following steps:

mixing and heating azelaic acid, succinic acid, and panthenol to obtain a liquid supramolecular self-recognition system of azelaic acid/succinic acid/panthenol with excellent water solubility and stability.

Further, the method for improving the water solubility and stability of azelaic acid includes the following steps:

mixing and heating azelaic acid, succinic acid, and panthenol in a molar ratio of 1:0.5:1-1:10:10 (mean 1:0.5-10:1-10) in a sealed container to obtain a mixture, heating the mixture at a temperature of 60-120° C. for more than 1 hour, and cooling down the mixture to room temperature after the heating is completed to obtain a ternary liquid supramolecular self-recognition system of azelaic acid/succinic acid/panthenol with excellent water solubility and stability.

Beneficial Effects (1) The present disclosure prepares a ternary liquid supramolecular self-recognition system of low-pH azelaic acid/succinic acid/panthenol using supramolecular self-recognition technology. The supramolecular self-recognition system can mix with water in a specific ratio without precipitation of azelaic acid, thereby significantly improving the solubility and stability of azelaic acid. Furthermore, a mass ratio of azelaic acid in the supramolecular self-recognition system can reach up to 42% (mass percentage), far higher than an actual application of azelaic acid, providing sufficient adjustment space for subsequent formulation application.

(2) The ternary liquid supramolecular self-recognition system of low-pH azelaic acid/succinic acid/panthenol prepared by the present disclosure can significantly enhance the water solubility of azelaic acid, and can be miscible with water. After miscibility, a mass concentration of azelaic acid can be as high as 30%, and no solid azelaic acid particles are precipitated.

(3) The ternary liquid supramolecular self-recognition system of low-pH azelaic acid/succinic acid/panthenol prepared by the present disclosure exhibits low viscosity and is transparent, and can be used directly or used s raw material. Moreover, the supramolecular self-recognition system has excellent long-term stability and performs well in formulation applications and product efficacy.

(4) Succinic acid in the ternary liquid supramolecular self-recognition system of low-pH azelaic acid/succinic acid/panthenol prepared by the present disclosure can effectively regulates a pH level of the system, and can provide a synergistic effect together with panthenol, such that the supramolecular self-recognition system has multiple benefits such as antibacterial and antiseptic, moisturizing, antioxidant, soothing, and repairing effects.

(5) The preparation method for the ternary liquid supramolecular self-recognition system of low-pH azelaic acid/succinic acid/panthenol provided in the present disclosure is green and simple, with mild preparation conditions, good atom economy, and no environmental issues of "three wastes" (waste gas, waste water, waste residual). Moreover, the supramolecular self-recognition system can be directly used without post-treatment such as separation and purification, making it suitable for large-scale preparation.

In summary, the preparation method for the ternary liquid supramolecular self-recognition system of low-pH azelaic acid/succinic acid/panthenol provided in the present disclosure is green and environmentally friendly, and has a simple process. It can significantly improve the solubility and stability of azelaic acid. By selecting appropriate compatible ingredients, the present disclosure can make the azelaic acid exhibit excellent performance in both raw material and formulation, which is of great significance for the application of azelaic acid and can expand its wide application in the fields of cosmetics and pharmaceuticals.

DETAILED DESCRIPTIONS OF THE EMBODIMENTS

Figure 1:
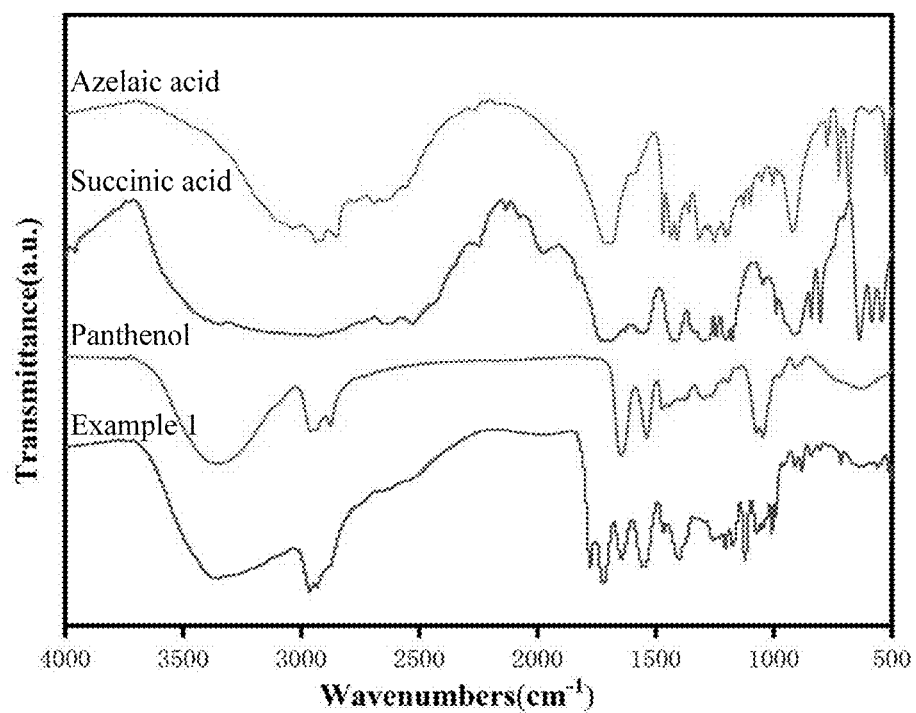
FIG. 1 is an infrared spectrogram of a ternary liquid supramolecular self-recognition system of low-pH azelaic acid/succinic acid/panthenol prepared according to Example 1 of the present disclosure.

The present disclosure provides a ternary liquid supramolecular self-recognition system for a low-pH azelaic acid/succinic acid/panthenol and examples of a preparation method therefor. Traditionally, due to poor water solubility, azelaic acid is difficult to evenly distribute in a water-based skincare product, which may result in unstable product, difficult to preserve, inefficient absorption by skin, thereby affecting the efficacy of the product. Therefore, it is necessary to take measures to increase the solubility of azelaic acid and improve product stability.

The present disclosure solves the problems well by using supramolecular self-recognition technology to change the water solubility and stability of azelaic acid by forming intermolecular hydrogen bonds. Meanwhile, by adjusting ratios and interactions among azelaic acid, succinic acid, and panthenol in the supramolecular self-recognition system, the present disclosure significantly enhances the applicability of azelaic acid, such that the azelaic acid can be evenly dispersed in the water-based skincare product, such that stability and absorbency of the product are increased, texture, stability, and performance of related products are improved, and user experience and functional effects of the products are finally improved.

The preparation method for the ternary liquid supramolecular self-recognition system of low-pH azelaic acid/succinic acid/panthenol includes the following steps:

mixing and heating azelaic acid, succinic acid, and panthenol to obtain a liquid supramolecular self-recognition system of low-pH azelaic acid.

A molar ratio of azelaic acid, succinic acid, and panthenol in the present disclosure is 1:0.5:1-1:10:10 (mean 1:0.5-10:1-10), preferably 1:1:1-1:8: 10 (mean 1:1-8:1-10), and most preferably 1:1:2-1:5:5 (mean 1:1-5:2-5)., and specifically 1:2:4, 1:3:5, or 1:1:2 in the examples of the present disclosure.

The mixing and heating in the present disclosure are performed in a sealed container.

The mixing and heating in the present disclosure are performed at a temperature of 60-120° C. for more than 1 hour; the temperature is preferably 70-120° C., and more preferably 90-110° C.; specifically, the temperature in the examples of the present disclosure can be 90° C., 100° C., and 110° C.; heating time is preferably 1-24 hours, further preferably 2-12 hours, and more preferably 2-5 hours; and specifically, the heating time can be 2 hours, 3 hours or 5 hours in the examples of the present disclosure.

A mixing and heating atmosphere in the present disclosure is an inert atmosphere or natural air conditions, and specifically helium, nitrogen, argon, or carbon dioxide; and specifically, the heating atmosphere in the examples of the present disclosure is natural air or nitrogen.

The mixing and heating in the present disclosure involve heating the mixture while stirring, a temperature rising rate during the heating is 1-10° C./minute. During the heating process, the mixture becomes liquid to form a liquid supramolecular self-recognition system, and a stirring speed is 200-1000 rpm; the a temperature rising rate is conventionally selected from 1-10° C./minute, and the a temperature rising rate in the examples is 3, 5, or 7° C./minute, and the stirring speed is selected from 200, 500, and 1000 rpm.

After the mixing and heating are completed, the mixture needs to be cooled down to room temperature, a cooling rate is generally selected from 1-10° C./minute, and the cooling rate for examples is selected from 5, 7, and 10° C./minute; and the room temperature ranges from 20-30° C., and the room temperatures for the examples in the present disclosure is 25° C.

A pH value of the ternary liquid supramolecular self-recognition system of low-pH azelaic acid is 2.5-5.5, and can specifically be 3.32, 4.67 or 4.36 for the examples in the present disclosure.

A mass fraction of azelaic acid in the ternary liquid supramolecular self-recognition system of low-pH azelaic acid/succinic acid/panthenol can reach 42%, and can specifically be 15%, 12% or 26% for the examples in the present disclosure.

The ternary liquid supramolecular self-recognition system of low-pH azelaic acid/succinic acid/panthenol provided in the present disclosure can significantly enhance the water solubility of azelaic acid, and can be miscible with water in a specific ratio, such that a mass ratio range of the ternary liquid supramolecular self-recognition system of low-pH azelaic acid/succinic acid/panthenol dissolved in water is 2:1-1:100 (mean 1-2:1-100); preferably 1:1-1:50 (mean 1:1-50), and more preferably 1:5-1: 20 (mean 1:5-20).; and specifically 1:5, 1:10 or 1:15 for the examples in the present disclosure.

The preferred examples of the present disclosure are described below, and it should be understood that the examples are intended for explaining the present disclosure better, rather than limiting the scope of the present disclosure.

Test Method

1. Fourier Transform Infrared Spectrometer Test:
   Instrument Model: FTS6000;
   The Manufacturer: Bio-Rad Laboratories Inc.;
   Experimental Parameters: Scanning range of 500-4000 $cm^{-1}$, resolution of 4 $cm^{-1}$.
2. Thermogravimetric Analyzer (TGA) Test:
   Instrument Model: Mettler TGA2 SF/1100;
   The Manufacturer: Mettler Toledo Pac Rim AG;
   Experimental Parameters: a temperature range of 25-450° C., a temperature rising rate of 10° C./minute, an experimental atmosphere of nitrogen and a flow rate of 50 mL/minute.
3. Antimicrobial Performance Test:
   Antimicrobial performance test includes preparation of a culture medium and an experimental bacterial solution. The culture medium is prepared in accordance with the *Cosmetics—Microbiology—Evaluation of the Antimicrobial Protection of a Cosmetic Product*. Preparation of the experiment bacterial solution includes: inoculating and amplifying standard strains on a culture medium, culturing the strains at 36° C. for 24 hours, adding to a elution solution of a corresponding concentration for elution, preparing a cell suspension containing approximately 108 standard bacteria per 1 mL using a turbidimetric method, and measuring a number of bacteria in each 1 mL of bacterial cell suspension if standard bacteria using a microbial limit test method. After appropriate bacterial colonies are cultured, a 28-day microbial performance test with one-time addition of bacteria is performed. 30 g of sample is added to each test sample. 1 portion of test bacterial solution (0.5 mL) is added to each test sample, and mixed thoroughly, samples are taken every 7, 14, and 28 days to measure bacterial counts in the samples and take their logarithm values for evaluation. Conditions for the samples to pass the antimicrobial performance test: a logarithmic value of a number of bacteria on the $14^{th}$ day reduces by no less than 2.0, and the number of bacteria during 14-28 days does not increase; otherwise, it should be considered that the antimicrobial performance test is not passed.
4. High-low temperature cycle test:
   Cycle storage at −5° C. and 40° C. is performed for 15 times; specifically, the supramolecular self-recognition system is frozen at-5° C. and then placed at 40° C. for dissolution, which constitutes one cycle, and the cycle is then repeated. Observe whether the supramolecular self-recognition system remains a stable, uniform liquid without solid precipitation after each cycle.

Raw Materials Used in the Examples

Panthenol is D-Panthenol or DL-panthenol, both of which are applicable to the present disclosure;

Particle size of azelaic acid: 500 nm-100 μm; particle size has no impact. Examples and Comparative Experiments use the azelaic acid with a particle size of 30 μm;

Fructooligosaccharide: 99%, molecular weight of 569, sourced from Shandong Yatu Biotechnology Co., Ltd.;

Marine Oligosaccharide: SEARUSHI Marine Oligosaccharide MGSD-II, sourced from Haisheng Health Technology (Qingdao) Co., Ltd.;

*Sphingomonas* sp. fermentation extract: Sourced from Shanghai Youshi Industrial Co., Ltd.;

Polyacryloyldimethyl taurate salt: 99%, sourced from Wuhan Lvjing Fenghua Biotechnology Co., Ltd.;

White willow bark extract: Sourced from Xi'an Plamed Green Science Group;

Ethylenediaminetetraacetic acid: 99%, sourced from Shanghai Yuanye Bio-Technology Co., Ltd.;

*Portulaca oleracea* extract: Sourced from Shanghai Huiwen Biotech Corp., Ltd.

Example 1

A preparation method for a ternary liquid supramolecular self-recognition system of low-pH azelaic acid/succinic acid/panthenol, including the following steps:

0.01 mol of azelaic acid, 0.02 mol of succinic acid, and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain the ternary liquid supramolecular self-recognition system of low-pH azelaic acid/succinic acid/panthenol, where a mass fraction of azelaic acid in the ternary liquid supramolecular self-recognition system of low-pH azelaic acid/succinic acid/panthenol was 15%, and a pH value measured by a pH meter was 4.36 (tested by a pH meter).

The prepared ternary liquid supramolecular self-recognition system of low-pH azelaic acid/succinic acid/panthenol was subjected to performance test, with test results as follows:

The prepared ternary liquid supramolecular self-recognition system of low-pH azelaic acid/succinic acid/panthenol was mixed evenly with water at a mass ratio of 1:10 to form a uniform transparent system, where a mass fraction of azelaic acid in an aqueous solution was 1.36%.

The prepared ternary liquid supramolecular self-recognition system of low-pH azelaic acid/succinic acid/panthenol and the uniform transparent system were subjected to high-low temperature cycle tests (stored at −5° C. and 40° C. for 15 cycles), respectively, and both systems were finally able to maintain a stable uniform liquid sate without any solid precipitation.

Figure 2:
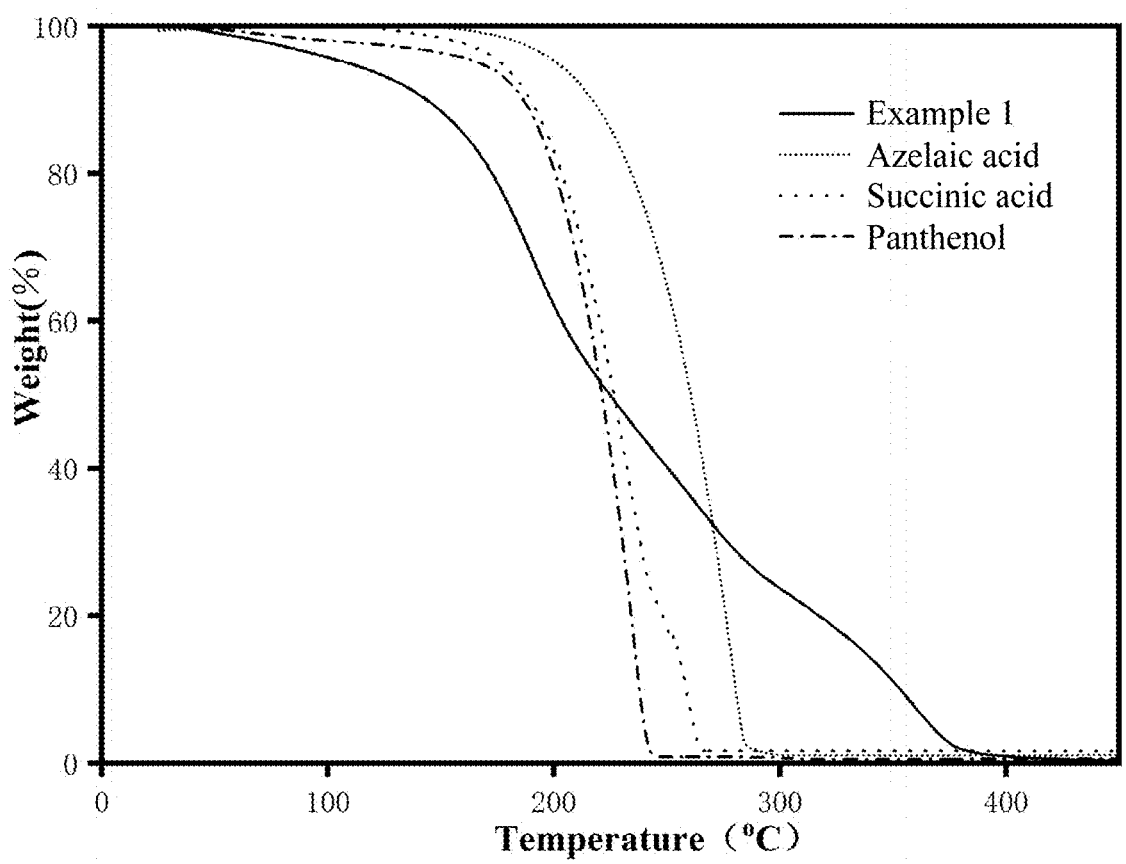
FIG. 2 is a thermogravimetric analysis curve of a ternary liquid supramolecular self-recognition system of low-pH azelaic acid/succinic acid/panthenol prepared according to Example 1 of the present disclosure.
Figure 3:
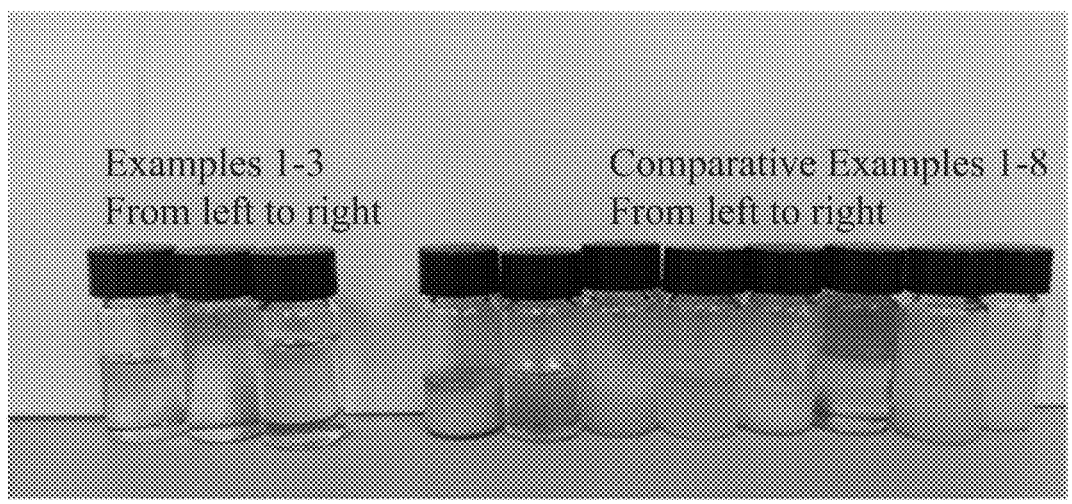
FIG. 3 is an appearance diagram of samples prepared in Examples 1-3 and Comparative Examples 1-8 after being placed for 24 hours.

After the ternary liquid supramolecular self-recognition system of low-pH azelaic acid/succinic acid/panthenol was stored at room temperature for 24 hours, samples were taken, and characterized by an infrared spectrometer and a thermogravimetric analyzer, with results shown in FIGS. 1 and 2:

FIG. 1 is an infrared spectrogram of the prepared ternary liquid supramolecular self-recognition system of low-pH azelaic acid/succinic acid/panthenol. As can be seen from FIG. 1, an absorption peak of the ternary liquid supramolecular self-recognition system of low-pH azelaic acid/ succinic acid/panthenol in a range of 3500-3200 $cm^{-1}$ corresponded to an absorption peak of a hydroxyl group (hydrogen bond), forming a broader peak. Compared with that of panthenol, a peak of the ternary liquid supramolecular self-recognition system of low-pH azelaic acid/succinic acid/panthenol shifted from 3355 $cm^{-1}$ to 3349 $cm^{-1}$ in a low wavenumber direction, indicating the a large number of hydrogen bonds were formed in the system and strong interaction occurred. In addition, compared with a carbonyl peak of single azelaic acid or succinic acid at 1690-1700 $cm^{-1}$, a peak of the ternary liquid supramolecular self-recognition system of low-pH azelaic acid/succinic acid/ panthenol increased at 1720 $cm^{-1}$, which resulted from changes in electron cloud density of carbonyl group caused by the generation of a large number of hydrogen bonds in the system. The above results further proved that azelaic acid, succinic acid, and panthenol could form a supramolecular self-recognition system through intermolecular hydrogen bonds.

FIG. 2 is a thermogravimetric analysis curve of the prepared ternary liquid supramolecular self-recognition system of low-pH azelaic acid/succinic acid/panthenol. As can be seen from FIG. 2, an initial weight loss temperature of the ternary liquid supramolecular self-recognition system of low-pH azelaic acid/succinic acid/panthenol was lower than that of the three individual components, and was closest to that of panthenol. In addition, the ternary liquid supramolecular self-recognition system of low-pH azelaic acid/ succinic acid/panthenol had a slower weight loss trend than that of the three individual components, indirectly indicating that the three components formed an organic entirety through hydrogen bonds.

Triple-distilled water (water subjected to three rounds of distillation and condensation) was added to the ternary liquid supramolecular self-recognition system of low-pH azelaic acid/succinic acid/panthenol to prepare a sample with an azelaic acid concentration of 0.5 mol/L for antimicrobial test, and test results were shown in Table 1.

TABLE 1

| Measurement Time (D) | Residual Bacterial Count (CFU/g) | | |
|---|---|---|---|
| | Escherichia coli | Pseudomonas aeruginosa | Staphylococcus aureus |
| 7 | <10 | $1*10^3$ | <10 |
| 14 | <10 | <10 | <10 |
| 28 | <10 | <10 | <10 |

As can be seen from Table 1, a count index of each of the Escherichia coli, Pseudomonas aeruginosa and Staphylococcus aureus decreased by more than 2.0 on the 14th day, and a bacterial count thereof did not increase from 14 to 28 days. Therefore, the samples passed the antibacterial challenge test, indicating that the samples had good efficacy in antibacterial performance.

Example 2

A preparation method for a ternary liquid supramolecular self-recognition system of low-pH azelaic acid/succinic acid/panthenol, including the following steps:

0.01 mol of azelaic acid, 0.03 mol of succinic acid, and 0.05 mol of D-Panthenol were placed in a sealed container, and the container was heated (3° C./minute, with a rotation speed of 200 rpm) slowly in a nitrogen atmosphere, and continuously heated for 2 hours after a temperature reached 110° C.; after heating was completed, and the container was cooled down to room temperature (7° C./minute, 25° C.) to obtain the ternary liquid supramolecular self-recognition system of low-pH azelaic acid/succinic acid/panthenol, where a mass fraction of azelaic acid in the ternary liquid supramolecular self-recognition system of low-pH azelaic acid/succinic acid/panthenol was 12%, and a pH value measured by a pH meter was 3.32 (tested by a pH meter).

The prepared ternary liquid supramolecular self-recognition system of low-pH azelaic acid/succinic acid/panthenol was subjected to performance test, with test results as follows:

The prepared ternary liquid supramolecular self-recognition system of low-pH azelaic acid/succinic acid/panthenol was mixed evenly with water at a mass ratio of 1:5 to form a uniform transparent system, where a mass fraction of azelaic acid in an aqueous solution was 2%.

The prepared ternary liquid supramolecular self-recognition system of low-pH azelaic acid/succinic acid/panthenol and the uniform transparent system were subjected to high-low temperature cycle tests (stored at −5° C. and 40° C. for 15 cycles), respectively, and both systems were finally able to maintain a stable uniform liquid sate without any solid precipitation.

Triple-distilled water (water subjected to three rounds of distillation and condensation) was added to the ternary liquid supramolecular self-recognition system of low-pH azelaic acid/succinic acid/panthenol to prepare a sample with an azelaic acid concentration of 0.5 mol/L for antimicrobial test, and test results were shown in Table 2.

TABLE 2

| Measurement Time (D) | Residual Bacterial Count (CFU/g) | | |
|---|---|---|---|
| | Escherichia coli | Pseudomonas aeruginosa | Staphylococcus aureus |
| 7 | 1*10³ | <10 | <10 |
| 14 | <10 | <10 | <10 |
| 28 | <10 | <10 | <10 |

As can be seen from Table 2, a count index of each of the *Escherichia coli, Pseudomonas aeruginosa* and *Staphylococcus aureus* decreased by more than 2.0 on the 14$^{th}$ day, and a bacterial count thereof did not increase from 14 to 28 days. Therefore, the samples passed the antibacterial challenge test, indicating that the samples had good efficacy in antibacterial performance.

Example 3

A preparation method for a ternary liquid supramolecular self-recognition system of low-pH azelaic acid/succinic acid/panthenol, including the following steps:

0.01 mol of azelaic acid, 0.01 mol of succinic acid, and 0.02 mol of DL-panthenol were placed in a sealed container, and the container was heated (10° C./minute, with a rotation speed of 1000 rpm) slowly in a natural air atmosphere, and continuously heated for 5 hours after a temperature reached 100° C.; after heating was completed, and the container was cooled down to room temperature (7° C./minute, 25° C.) to obtain the ternary liquid supramolecular self-recognition system of low-pH azelaic acid/succinic acid/panthenol, where a mass fraction of azelaic acid in the ternary liquid supramolecular self-recognition system of low-pH azelaic acid/succinic acid/panthenol was 26%, and a pH value measured by a pH meter was 4.67 (tested by a pH meter).

The prepared ternary liquid supramolecular self-recognition system of low-pH azelaic acid/succinic acid/panthenol was subjected to performance test, with test results as follows:

The prepared ternary liquid supramolecular self-recognition system of low-pH azelaic acid/succinic acid/panthenol was mixed evenly with water at a mass ratio of 1:15 to form a uniform transparent system, where a mass fraction of azelaic acid in an aqueous solution was 1.6%.

The prepared ternary liquid supramolecular self-recognition system of low-pH azelaic acid/succinic acid/panthenol and the uniform transparent system were subjected to high-low temperature cycle tests (stored at −5° C. and 40° C. for 15 cycles), respectively, and both systems were finally able to maintain a stable uniform liquid sate without any solid precipitation.

Triple-distilled water (water subjected to three rounds of distillation and condensation) was added to the ternary liquid supramolecular self-recognition system of low-pH azelaic acid/succinic acid/panthenol to prepare a sample with an azelaic acid concentration of 0.5 mol/L for antimicrobial test, and test results were shown in Table 3.

TABLE 3

| Measurement Time (D) | Residual Bacterial Count (CFU/g) | | |
|---|---|---|---|
| | Escherichia coli | Pseudomonas aeruginosa | Staphylococcus aureus |
| 7 | 1*10³ | 1*10³ | <10 |
| 14 | <10 | <10 | <10 |
| 28 | <10 | <10 | <10 |

As can be seen from Table 3, a count index of each of the *Escherichia coli, Pseudomonas aeruginosa* and *Staphylococcus aureus* decreased by more than 2.0 on the 14$^{th}$ day, and a bacterial count thereof did not increase from 14 to 28 days. Therefore, the samples passed the antibacterial challenge test, indicating that the samples had good efficacy in antibacterial performance.

Example 4

A preparation method for a ternary liquid supramolecular self-recognition system of low-pH azelaic acid/succinic acid/panthenol, including the following steps:

0.01 mol of azelaic acid, 0.02 mol of succinic acid, and 0.04 mol of DL-panthenol were placed in a sealed container, and the container was heated (5° C./minute, with a rotation speed of 500 rpm) slowly in a natural air atmosphere, and continuously heated for 1 hour after a temperature reached 70° C.; after heating was completed, and the container was cooled down to room temperature (5° C./minute, 25° C.) to obtain the ternary liquid supramolecular self-recognition system of low-pH azelaic acid/succinic acid/panthenol, where a mass fraction of azelaic acid in the ternary liquid supramolecular self-recognition system of low-pH azelaic acid/succinic acid/panthenol was 15%, and a pH value measured by a pH meter was 4.35 (tested by a pH meter).

The prepared ternary liquid supramolecular self-recognition system of low-pH azelaic acid/succinic acid/panthenol was mixed evenly with water at a mass ratio of 1:10 to form a uniform transparent system, where a mass fraction of azelaic acid in an aqueous solution was 1.36%.

Figure 4A:
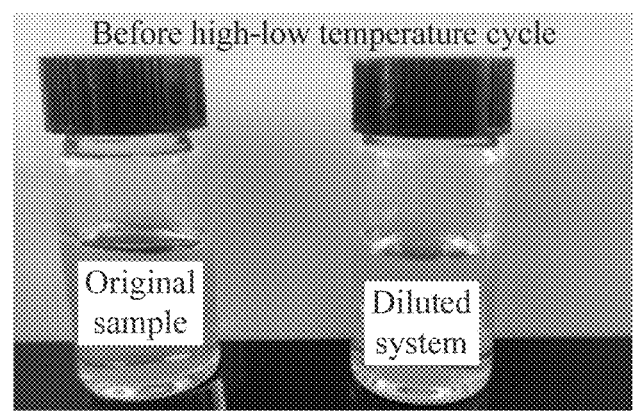
FIG. 4A shows test results before high-low temperature cycle of samples prepared in Example 4.
Figure 4B:
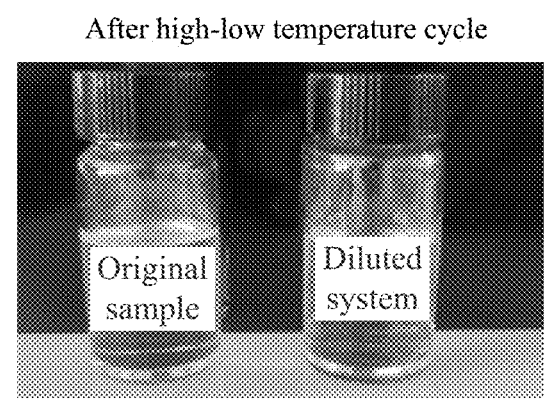
FIG. 4B shows test results after high-low temperature cycle of samples prepared in Example 4.

The prepared ternary liquid supramolecular self-recognition system of low-pH azelaic acid/succinic acid/panthenol and the uniform transparent system were subjected to high-low temperature cycle tests (stored at −5° C. and 40° C. for 15 cycles), respectively, and both systems were finally able to maintain a stable uniform liquid sate without any solid precipitation (A picture of physical object was shown in FIG. 4A and FIG. 4A).

Example 5

A preparation method for a ternary liquid supramolecular self-recognition system of low-pH azelaic acid/succinic acid/panthenol, including the following steps:

0.01 mol of azelaic acid, 0.02 mol of succinic acid, and 0.04 mol of DL-panthenol were placed in a sealed container, and the container was heated (5° C./minute, with a rotation speed of 500 rpm) slowly in a natural air atmosphere, and continuously heated for 12 hours after a temperature reached 60° C.; after heating was completed, and the container was cooled down to room temperature (5° C./minute, 25° C.) to obtain the ternary liquid supramolecular self-recognition system of low-pH azelaic acid/succinic acid/panthenol, where a mass fraction of azelaic acid in the ternary liquid supramolecular self-recognition system of low-pH azelaic acid/succinic acid/panthenol was 15%, and a pH value measured by a pH meter was 4.35 (tested by a pH meter).

The prepared ternary liquid supramolecular self-recognition system of low-pH azelaic acid/succinic acid/panthenol was mixed evenly with water at a mass ratio of 1:10 to form a uniform transparent system, where a mass fraction of azelaic acid in an aqueous solution was 1.36%.

The prepared ternary liquid supramolecular self-recognition system of low-pH azelaic acid/succinic acid/panthenol and the uniform transparent system were subjected to high-low temperature cycle tests (stored at −5° C. and 40° C. for 15 cycles), respectively, and both systems were finally able to maintain a stable uniform liquid sate without any solid precipitation.

Comparative Example 1

This Comparative Example was substantially the same as Example 1, except that panthenol was not used but succinic acid was used, and specific operation was as follows:

0.01 mol of azelaic acid and 0.02 mol of succinic acid were mixed and placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when the succinic acid was used only as a single compatible molecule for supramolecular self-recognition, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 2

This Comparative Example was substantially the same as Example 1, except that succinic acid was not used but panthenol was used, and specific operation was as follows:

0.01 mol of azelaic acid and 0.04 mol of DL-panthenol were mixed and placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

The product was subjected to test, with test results as follows:

The product was a uniform, transparent and stable liquid system; the product was mixed with water at a mass ratio of 1:10 to obtain a uniform and transparent aqueous solution; and triple-distilled water was added to the product to prepare a sample with an azelaic acid concentration of 0.5 mol/L for antimicrobial test, and test results were shown in Table 4.

TABLE 4

| Measurement Time (D) | Residual Bacterial Count (CFU/g) | | |
|---|---|---|---|
| | Escherichia coli | Pseudomonas aeruginosa | Staphylococcus aureus |
| 7 | $3*10^2$ | $2*10^3$ | <10 |
| 14 | <10 | <10 | <10 |
| 28 | <10 | <10 | <10 |

As can be seen from Table 4, a count index of each of the *Escherichia coli, Pseudomonas aeruginosa* and *Staphylococcus aureus* decreased by more than 2.0 on the $14^{th}$ day, and a bacterial count thereof did not increase from 14 to 28 days. The system also exhibited a certain bactericidal capability. However, compared with Example 1, residual bacterial counts of Escherichia coli and Pseudomonas aeruginosa from 0 to 7 days were significantly higher than those tested in Example 1, which was more than 2-3 times the bacterial counts in Example 1. It can be seen that the introduction of succinic acid in the system of Example 1 significantly enhanced antiseptic and antibacterial properties of the system, exhibiting good bactericidal performance in a short period of time.

Comparative Example 3

This Comparative Example was substantially the same as Example 1, except that a use amount of succinic acid was increased, and specific operation was as follows:

0.01 mol of azelaic acid, 0.11 mol of succinic acid and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when the use amount of succinic acid was increased alone, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 4

This Comparative Example was substantially the same as Example 1, except that a use amount of azelaic acid was increased, and specific operation was as follows:

0.05 mol of azelaic acid, 0.02 mol of succinic acid and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when the use amount of azelaic acid was increased alone, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 5

This Comparative Example was substantially the same as Example 1, except that a heating temperature was lowered, and specific operation was as follows:

0.01 mol of azelaic acid, 0.02 mol of succinic acid and 0.04 mol of DL-panthenol were placed in a sealed container, and the container was heated (5° C./minute, with a rotation speed of 500 rpm) slowly in a natural air atmosphere, and continuously heated for 3 hours after a temperature reached 50° C.; after heating was completed, and the container was cooled down to room temperature (5° C./minute, 25° C.) to obtain a product.

Results indicated that when the heating temperature was lowered, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 6

This Comparative Example was substantially the same as Example 1, except that a heating temperature was raised, and specific operation was as follows:

0.01 mol of azelaic acid, 0.02 mol of succinic acid and 0.04 mol of DL-panthenol were mixed and placed in a sealed container, and the container was heated (5° C./minute, with a rotation speed of 500 rpm) slowly in a natural air atmosphere, and continuously heated for 3 hours after a temperature reached 130° C.; after heating was completed, and the container was cooled down to room temperature (5° C./minute, 25° C.) to obtain a product.

Results indicated that when the heating temperature was raised, a uniform, transparent and stable liquid system can be obtained, and the system turned into a dark yellow liquid system after being placed at room temperature for 24 hours. Deepening of the system color suggested that a chemical reaction had occurred, that is, new covalent bonds rather than hydrogen bonds have been generated. The solid-liquid mixture after being placed at room temperature for 24 hours was mixed with water at a mass ratio of 1:10, a uniform and transparent aqueous solution could not be obtained, but an insoluble oily substance floated on a water layer.

Comparative Example 7

This Comparative Example was substantially the same as Example 1, except that heating time was shortened, and specific operation was as follows:

0.01 mol of azelaic acid, 0.02 mol of succinic acid and 0.04 mol of DL-panthenol were mixed and placed in a sealed container, and the container was heated (5° C./minute, with a rotation speed of 500 rpm) slowly in a natural air atmosphere, and continuously heated for 45 minutes after a temperature reached 90° C.; after heating was completed, and the container was cooled down to room temperature (5° C./minute, 25° C.) to obtain a product.

Results indicated that when the heating time was shortened, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 8

This Comparative Example was substantially the same as Example 1, except that succinic acid was replaced by disodium succinate, and specific operation was as follows:

0.01 mol of azelaic acid, 0.02 mol of disodium succinate and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when succinic acid was replaced by disodium succinate, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered. Compared with Example 1, when succinic acid was replaced by disodium succinate, a supramolecular self-recognition system could not be obtained, indicating that the hydroxyl group of succinic acid in Example 1 participated in the supramolecular hydrogen bonding.

Comparative Example 9

This Comparative Example was substantially the same as Example 1, except that succinic acid was replaced by diethyl succinate, and specific operation was as follows:

0.01 mol of azelaic acid, 0.02 mol of diethyl succinate and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when succinic acid was replaced by diethyl succinate, a uniform, transparent and stable liquid system could not be obtained. After being placed at room temperature for 24 hours, the system turned into white cream. The white cream after being placed at room temperature for 24 hours was mixed with water at a mass ratio of 1:10, a uniform and transparent aqueous solution could not be obtained, but solid insoluble was precipitated at a bottom of the system and oily substances floated on a top layer of the system. Compared with Example 1, when succinic acid was replaced by diethyl succinate, a supramolecular self-recognition system could not be obtained, indicating that the hydroxyl group of succinic acid in Example 1 participated in the supramolecular hydrogen bonding.

Comparative Example 10

This Comparative Example was substantially the same as Example 1, except that succinic acid was replaced by adipic acid, and specific operation was as follows:

0.01 mol of azelaic acid, 0.02 mol of adipic acid and 0.04 mol of DL-panthenol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when succinic acid was replaced by adipic acid, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered. Compared with Example 1, succinic acid was replaced by adipic acid. Adipic acid also had effects similar to succinic acid such as such as antimicrobial and pH regulation. In addition, adipic acid contained hydroxyl groups and was very similar in structure to that of succinic acid, and could also form supramolecular hydrogen bonds theoretically. However, adipic acid could not form a supramolecular self-recognition system, indicating that succinic acid as a compatible molecule in the self-recognition system of the present disclosure had a high degree of selectivity.

Comparative Example 11

This Comparative Example was substantially the same as Example 1, except that panthenol was replaced by polyethylene glycol 400, and specific operation was as follows:

0.01 mol of azelaic acid, 0.02 mol of succinic acid and 0.04 mol of polyethylene glycol 400 were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when panthenol was replaced by polyethylene glycol 400, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 12

This Comparative Example was substantially the same as Example 1, except that panthenol was replaced by propylene glycol, and specific operation was as follows:

0.01 mol of azelaic acid, 0.02 mol of succinic acid and 0.04 mol of propylene glycol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when panthenol was replaced by propylene glycol, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Comparative Example 13

This Comparative Example was substantially the same as Example 1, except that panthenol was replaced by a mixture of polyethylene glycol 400 and propylene glycol (with a mass ratio of 3:1), and specific operation was as follows:

0.01 mol of azelaic acid, 0.02 mol of succinic acid and 0.04 mol of the mixture of polyethylene glycol 400 and propylene glycol were placed in a sealed container, and the container was heated (5° C./minute, with a rotation speed of 500 rpm) slowly in a natural air atmosphere, and continuously heated for 3 hours after a temperature reached 90° C.; after heating was completed, and the container was cooled down to room temperature (5° C./minute, 25° C.) to obtain a product.

Results indicated that when succinic acid was replaced by the mixture of polyethylene glycol 400 and propylene glycol with a mass ratio of 3:1, a uniform, transparent and stable liquid system could not be obtained. After being placed at room temperature for 24 hours, the system turned into a solid-liquid mixture. The solid-liquid mixture after being placed at room temperature for 24 hours was mixed with water at a mass ratio of 1:10, a uniform and transparent aqueous solution could not be obtained, but solid insoluble were discovered.

Example 6 Application in Cosmetics

The ternary liquid supramolecular self-recognition system for the low-pH azelaic acid/succinic acid/panthenol prepared in Example 6 was applied in the preparation of a cosmetic product, with specific formulation shown in Table 5.

TABLE 5

Serum Formulation

| S/N | Ingredient | % w/w |
|---|---|---|
| 1 | Water | To 100 |
| 2 | Glycerin | 3 |
| 3 | Butanediol | 3 |
| 4 | Phenoxyethanol | 0.4 |
| 5 | 1,2-Octanediol | 0.4 |
| 6 | *Sphingomonas sp.* Fermentation Extract | 0.1 |
| 7 | Sodium hyaluronate | 0.05 |
| 8 | Polyacryloyldimethyl taurate salt | 0.1 |
| 9 | Supramolecular self-recognition system in Example 1 | 20 |
| 10 | White willow bark extract | 2 |
| 11 | Ethylenediaminetetraacetic acid | 0.05 |
| 12 | *Portulaca oleracea* extract | 2 |

A preparation method for the serum was as follows:

Ingredients No. 1-5 and No. 11 were added into a main vessel and mixed until the ingredients were dissolved, and heated to 75° C.; ingredients No. 6-8 were added into the main vessel and stirred evenly, and cooled down to 45° C.; and ingredients No. 9, 10 and 12 were added and stirred evenly, and the preparation of serum was completed.

The prepared serum was tested for stability in accordance with GB/T 26367-2010, and test results indicated that the stability requirements were satisfied. Further, the prepared serum had moisturizing and acne-removing effects.

Comparative Example 14

According to the serum formulation in Table 5, the supramolecular self-recognition system obtained in Example 1 was replaced with 1.55% w/w of azelaic acid and 3.45% w/w of DL-panthenol, and the serum was prepared according to formulation in Table 6 below.

TABLE 6

Serum Formulation

| S/N | Ingredient | % w/w |
|---|---|---|
| 1 | Water | To 100 |
| 2 | Glycerin | 3 |
| 3 | Butanediol | 3 |
| 4 | Phenoxyethanol | 0.4 |

TABLE 6-continued

Serum Formulation

| S/N | Ingredient | % w/w |
| --- | --- | --- |
| 5 | Caprylyl glycol | 0.4 |
| 6 | *Sphingomonas sp.* Fermentation Extract | 0.1 |
| 7 | Sodium hyaluronate | 0.05 |
| 8 | Polyacryloyldimethyl taurate salt | 0.1 |
| 9 | Azelaic acid | 3 |
| 10 | Succinic acid | 3.8 |
| 11 | DL-panthenol | 13.2 |
| 12 | White willow bark extract | 2 |
| 13 | Ethylenediaminetetraacetic acid | 0.05 |
| 14 | *Portulaca oleracea* extract | 2 |

A preparation method for the serum was as follows:

Ingredients No. 1-5 and No. 13 were added into a main vessel and dissolved evenly, and heated to 75° C.; ingredients No. 6-8 were added into the main vessel and stirred evenly, and cooled down to 45° C.; and ingredients No. 9-12 and 14 were added and stirred evenly, and the preparation of serum was completed.

The prepared serum was tested for stability in accordance with GB/T 26367-2010, and test results indicated that the stability was unqualified and solids were precipitated.

Example 7 Application in Pharmaceuticals

The ternary liquid supramolecular self-recognition system for the low-pH azelaic acid/succinic acid/panthenol prepared in Example 1 was applied in the preparation of acne treatment gel, and specific formulation was shown in Table 7.

TABLE 7

Gel Formulation

| S/N | Ingredient | % w/w |
| --- | --- | --- |
| 1 | Water | To 100 |
| 2 | Docusate sodium | 0.05 |
| 3 | Disodium edetate | 0.1 |
| 4 | Glycerin | 4 |
| 5 | Poloxamer 124 | 0.2 |
| 6 | Propylene glycol | 4 |
| 7 | SIMULGEL 600PHA | 4 |
| 8 | Supramolecular self-recognition system in Example 1 | 30 |

A preparation method was as follows:

(1) Preparation of an Active Phase:

Poloxamer 124 was added to water and stirred evenly to obtain a mixture, the mixture was continuously stirred until it completely dissolved and became clear, the supramolecular self-recognition system prepared in Example 1 was then added and stirred homogenously at 10000 rpm with a homogenizer for 30 minutes for later use;

(2) Preparation of an Aqueous Phase:

propylene glycol and glycerin were added to water and dissolved until clear, and docusate sodium was then added and stirred at 1000 rpm until clear for later use;

(3) Mixing:

the aqueous phase and the active phase were added in a vessel in sequence, an active phase beaker was rinsed with water, and SIMULGEL 600PHA was added and stirred homogenously at 2800 rpm for 45 minutes;

(4) Filling:

Gel was manually filled into an empty plastic tube to obtain the acne treatment gel.

The resulting gel was subjected to stability test, and test results showed that the stability was acceptable, without solid precipitation, and it exhibited some efficacy in treating acne.

Although the present disclosure has been disclosed as above in the form of preferred embodiments, it is not intended to limit the present disclosure. Those skilled in the art can make various modifications and variations without departing from the spirit and scope of the present disclosure. Therefore, the scope of protection of the present disclosure should be defined by the claims.

What is claimed is:

1. A method for preparing a ternary liquid supramolecular self-recognition system of azelaic acid, succinic acid, and panthenol, which comprises:

mixing and heating azelaic acid, succinic acid, and panthenol to obtain a liquid supramolecular self-recognition system of low-pH azelaic acid, wherein low-pH indicates a pH value of the ternary liquid supramolecular self-recognition system of 2.5 to 5.5, wherein a molar ratio of the azelaic acid to the succinic acid to the panthenol is 1:0.5:1 to 1:10:10, and wherein the mixing and heating are performed at a temperature of 60° C. to 120° C. for more than 1 hour.

2. The method according to claim 1, further comprising cooling down the mixture to room temperature after the heating is completed to obtain the liquid supramolecular self-recognition system of low-pH azelaic acid.

3. The method according to claim 1, wherein the mixing and heating comprises heating the mixture while stirring.

4. The method according to claim 1, wherein a temperature rising rate during the heating is 1° C. to 10° C. per minute, and a stirring speed is 200 rpm to 1000 rpm.

5. The method according to claim 2, wherein a cooling rate is 1° C. to 10° C. per minute.

6. The method according to claim 1, wherein a mixing and heating atmosphere is an inert atmosphere or natural air conditions.

7. The method according to claim 6, wherein the mixing and heating atmosphere is helium, nitrogen, argon, carbon dioxide, or natural air.

8. A method for preparing a ternary liquid supramolecular self-recognition system of azelaic acid, succinic acid, and panthenol, which comprises:

mixing and heating azelaic acid, succinic acid, and panthenol to obtain a liquid supramolecular self-recognition system of low-pH azelaic acid with excellent water solubility and stability;

wherein low-pH indicates a pH value of the ternary liquid supramolecular self-recognition system of 2.5 to 5.5, wherein a molar ratio of the azelaic acid to the succinic acid to the panthenol is 1:0.5:1 to 1:10:10, wherein a temperature rising rate during the heating is 1° C. to 10° C. per minute, and a stirring speed is 200 rpm to 1000 rpm, wherein a cooling rate is 1° C. to 10° C. per minute, and wherein the mixing and heating are performed at a temperature of 60° C. to 120° C. for more than 1 hour.

\* \* \* \* \*